United States Patent
Shen et al.

(10) Patent No.: US 8,697,918 B2
(45) Date of Patent: Apr. 15, 2014

(54) INTERMEDIATE OF LYCOPENE AND PREPARATION METHOD OF INTERMEDIATE

(71) Applicants: ZheJiang Medicine Co., Ltd. Xinchang, (CN); Zhaoxing University, (CN)

(72) Inventors: Runpu Shen, Xinchang County (CN); Chunlei Lv, Xinchang County (CN); Xiaoyue Jiang, Xinchang County (CN); Xuejun Lao, Xinchang County (CN); Weidong Ye, Xinchang County (CN); Luo Liu, Xinchang County (CN); Xiaohua Song, Xinchang County (CN); Chunlei Wu, Xinchang County (CN)

(73) Assignees: Shaoxing University, Zhejiang Province (CN); Zhejiang Medicine Co., Ltd. Xinchang Pharmaceutical Factory, Zheijang Province (CN)

( * ) Notice: Subject to any disclaimer, the term of this patent is extended or adjusted under 35 U.S.C. 154(b) by 0 days.

(21) Appl. No.: 13/692,658

(22) Filed: Dec. 3, 2012

(65) Prior Publication Data
US 2014/0005442 A1 Jan. 2, 2014

Related U.S. Application Data

(63) Continuation of application No. PCT/CN2011/000154, filed on Jan. 30, 2011.

(51) Int. Cl.
*C07C 45/00* (2006.01)
(52) U.S. Cl.
USPC ............................................. 568/429
(58) Field of Classification Search
USPC ............................................. 568/429
See application file for complete search history.

(56) References Cited

U.S. PATENT DOCUMENTS 4,675,451 A * 6/1987 Andrade et al. .............. 568/486
5,973,179 A * 10/1999 Babler et al. .................... 558/83

OTHER PUBLICATIONS

Valla et al. New Synthesis of Retinal and Its Acyclic gamma-Retinal by an Extended Aldol Reaction with a C6 Building Block That Incorporates a C5 Unit After Decarboxylation. A Formal Route to Lycopene and Beta-Carotene. Helvetica Chemica Acta, 2007, vol. 90, pp. 512-520.*

* cited by examiner

*Primary Examiner* — Sikarl Witherspoon
(74) *Attorney, Agent, or Firm* — Daniel A. Thomson; Emerson Thomson Bennett, LLC

(57) ABSTRACT

The present invention relates to 2,6,10-trimethyl-3,5,9-undecatrienyl-1-aldehyde represented by formula (3), and a method for preparing this intermediate. The process route of the present invention is simple, the starting materials are available easily, and the cost is low.

17 Claims, No Drawings

INTERMEDIATE OF LYCOPENE AND PREPARATION METHOD OF INTERMEDIATE

FIELD OF THE INVENTION

This present invention relates to a method of preparing an intermediate of lycopene of 2,6,10-trimethyl-3,5,9-undecatrienyl-1-aldehyde.

BACKGROUND OF THE INVENTION

There are approximately 600 kinds of carotenoids naturally, but only six kinds of these have so far been produced industrially such as production by Roche Corporation and BASF Corporation. Lycopene as an important product has important functions on scavenging free radical, antiageing, inhibiting tumor, treating heart attack and so on (H. Gerster, J. Am. Coll. Nutr. 1997, 16, 109; Nutr. Cancer 1995, 24.257; E. Giovannucci. et al. J. Natl. Cancer Inst. 1995, 87, 1767; Chem. Abstracts 1990, 112 91375w), and is widely used for medicines, food additives, feed additives. Roche Corporation develops a synthesis route by the Witting Reaction, wherein it uses expensive and poisonous raw materials such as tri-phenyl phosphorous (K. Meyer, et al., Helv. Chim. Acta 1992, 75.1848). Other former synthesis methods use tri-phenyl phosphorous either (P. Karrer, et al., Helv. Chim. Acta 1950, 33, 1349; B. C. L. Weedon, et al., J. Chem. Soc. 1965, 2019; K. Bernhard and H. Mayer, Pure & Appl.-them. 1991, 63, 35).

It has been reported from Publication No. WO 0031086 (2000 Jun. 2) of PCT application that Babler J. H. et al. developed a new method of synthesizing lycopene by the Wittig-Horner Reaction, wherein 3,7,11-trimethyl-2,4,6,10-dodecatetraenyl phosphonic acid diethyl ester of formula (5) as a crucial intermediate undergoes a condensation reaction with decyl di-aldehyde (8) by catalysis of bases for preparing lycopene, the whole synthesis sequence is described as follows.

Firstly, pseudoionone (2) reacts with ethynyl anion to produce tertiary alcohol (7) (3,7,11-trimethyl-4,6,10-dodecatrien-1-yn-3-ol):

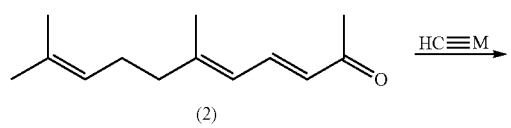

(2)

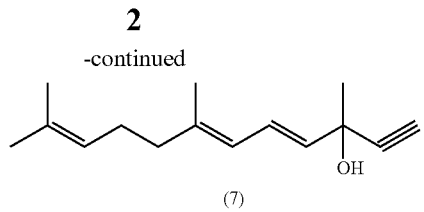

(7)

Afterwards, tertiary alcohol (7) reacts with dialkyl chlorophosphite to produce propadiene pentadecyl phosphoric acid ester (6) (3,7,11-trimethyl-1,2,4,6,10-dodecapentaenyl phosphoric acid diethyl ester).

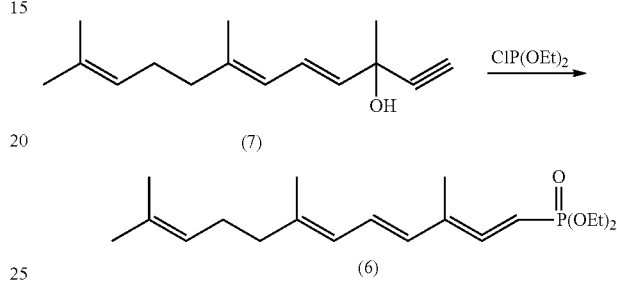

Secondly, propadiene pentadecyl phosphoric acid ester (6) is partially reduced and transformed to pentadecyl phosphoric acid ester (5) (3,7,11-,trimethyl-2,4,6,10-dodecatetraenyl phosphoric acid diethyl ester):

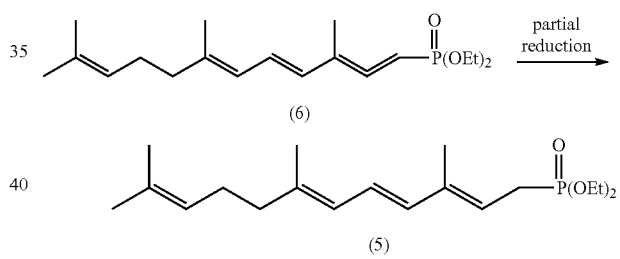

Finally, pentadecyl phosphoric acid ester (5) undergoes a condensation reaction with decanal di-aldehyde (8) (2,7-dimenthyl-2,4,6-octatriene-1,8-dial) by catalysis of bases to obtain lycopene (1).

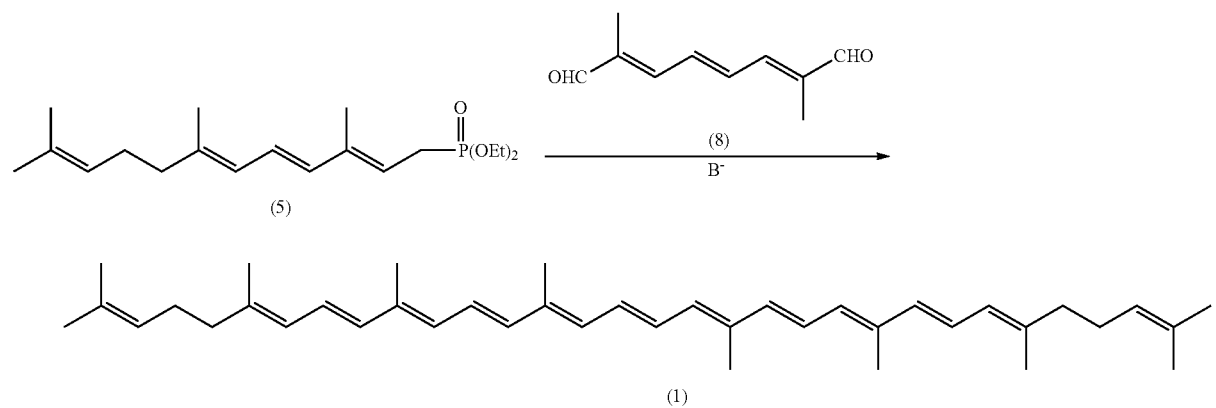

The method uses a new compound 2,4,6,10-pentadecatetraenyl phosphoric acid ester (5) as an intermediate to avoid uses of triphenyl phosphorous; and moreover uses pseudoionone as a raw material to obtain products of lycopene by reactions of four steps. The synthesis route thereof is concise, and has prominent improvement relative to former methods. However there are some problems in the method. Firstly it is difficulty for reactions of tertiary alcohol (7) with dialkyl chlorophosphite to produce propadiene pentadecyl phosphoric acid ester (6). Secondly it is hard to handle the reduction technology of propadiene pentadecyl phosphoric acid ester (6) selectively being reduced to pentadecyl phosphoric acid ester (5).

Recently, the Chinese patent application No. 2010101042817 of Runbo SHEN et. al. discloses a method of preparing lycopene (1) by a condensation reaction of Wittig-Horner between 1,4,6,10-tetra-double bond pentadec-carbon phosphonate of formula (4) (3,7,11-,trimethyl-1,4,6,10-dodecatetraenyl phosphoric acid diethyl ester) and decanal di-aldehyde (8). The synthesis route of the method comprises the following reaction sequence:

dimethyl sulfide and dangerous DMSO sodium, and is difficult to apply for industrial production.

SUMMARY OF THE INVENTION

In order to overcome these deficiencies in the prior art, the first objective of the present invention is to provide an intermediate of lycopene, 4-methyl-5,5-dialkoxy-1-pentenyl-1-phosphoric acid dialkyl ester of formula (10):

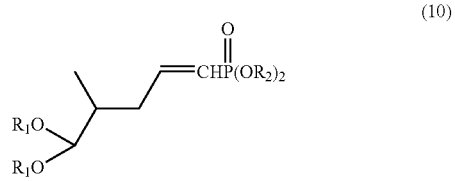

wherein $R_1$ and $R_2$ are $C_{1-4}$ alkyl.

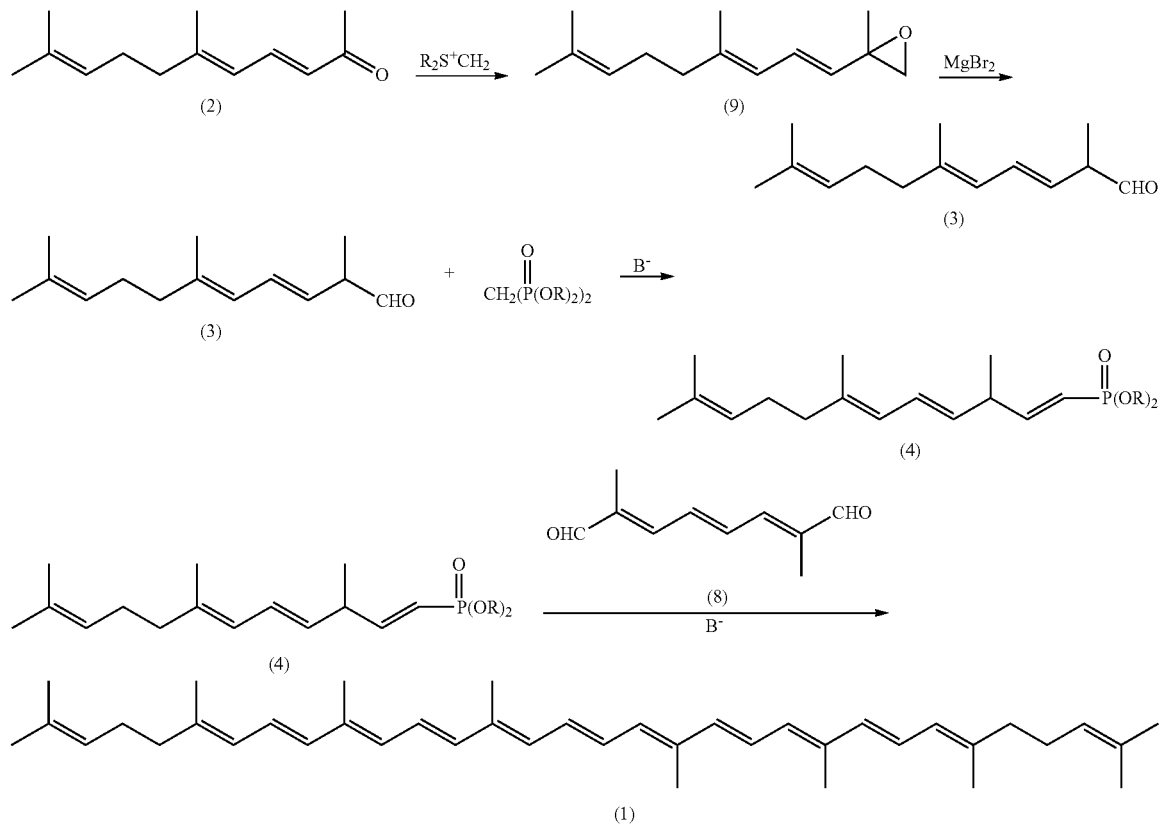

The method of preparing the key intermediate C-14 aldehyde [2,6,10-trimethyl-3,5,9-undecatrienyl-1-aldehyde of formula (3)] refers to the U.S. Pat. No. 4,000,131 (Rosenberger, et al., Oct. 28, 1976). That is, 2,6,10-trimethyl-3,5,9-undecatrienyl-1-aldehyde of formula (3) is obtained by reaction of pseudoionone (2) reacts with sulfonium salt to produce epoxide, and then the epoxide is catalyzed to open a loop to obtain 3-position double bond of formula (3), 2,6,10-trimethyl-3,5,9-undecatrienyl-1-aldehyde. However this method has deficiencies of expensive iodomethane, polluted The second objective of the present invention is to provide a method of preparing 4-methyl-5,5-dialkoxy-1-pentenyl-1-phosphoric acid dialkyl ester of formula (10). The method comprises the following steps: undergoing a Wittig-Horner condensation reaction of 3-methyl-4,4-dialkoxy-1-aldehyde of formula (11) with tetra-alkyl methylene diphosphonate at temperature of 0~30° C. in ether solvent or dipolar aprotic solvent and under protection of inert gases and in the presence of bases to produce 4-methyl-5,5-dialkoxy-1-pentenyl-1-phosphoric acid dialkyl ester of formula (10). The reaction sequence is described as follows:

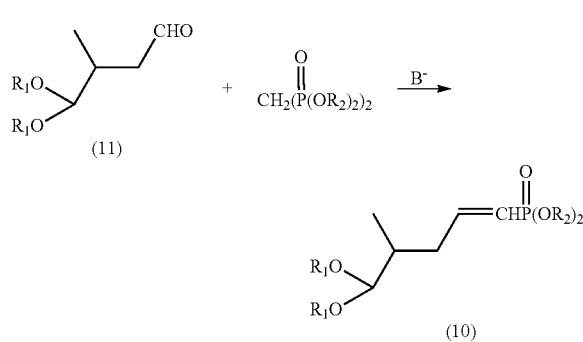

wherein $R_1$ and $R_2$ are $C_{1-4}$ alkyl.

The third objective of the present invention is to provide another intermediate of lycopene, 2,6,10-trimethyl-1,1-dialkoxy-3,5,9-undecan-triene of formula (12):

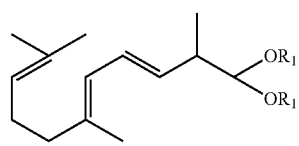

wherein $R_1$ is $C_{1-4}$ alkyl.

The fourth purpose of the present invention is to provide a method of preparing 2,6,10-trimethyl-1,1-dialkoxy-3,5,9-undecantriene of formula (12). The method comprises the following steps:

Step (1): 4-methyl-5,5-dialkoxy-1-pentenyl-1-phosphoric acid dialkyl ester of formula (10) undergoes a rearrangement reaction, at temperature of −40~30° C. in ether solvent or dipolar aprotic solvent and under protection of inert gas in the presence of bases;

Step (2): 6-methyl-5-heptene-2-one of formula (13) is added to undergo a Wittig-Horner condensation reaction to produce 2,6,10-trimethyl-1,1-dialkoxy-3,5,9-undecan-triene of formula (12), at temperature of −40~30° C. in ether solvent or dipolar aprotic solvent and in the presence of bases. The reaction sequence is described as follows:

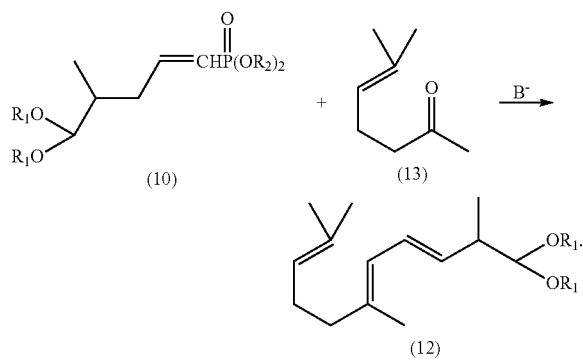

The fifth objective of this invention is to provide a method of preparing 2,6,10-trimethyl-3,5,9-undecatrienyl-1-aldehyde of formula (3) by using 2,6,10-trimethyl-1,1-dialkoxy-3,5,9-undecantriene of formula (12). The method comprises the following steps: mixing 2,6,10-trimethyl-1,1-dialkoxy-3,5,9-undecantriene of formula (12) with acid catalyst, water and homogeneous solvent, at the temperature of 10-35° C. under the protection of inert gas, and undergoing a hydrolysis reaction. Its reaction sequence is described as follows:

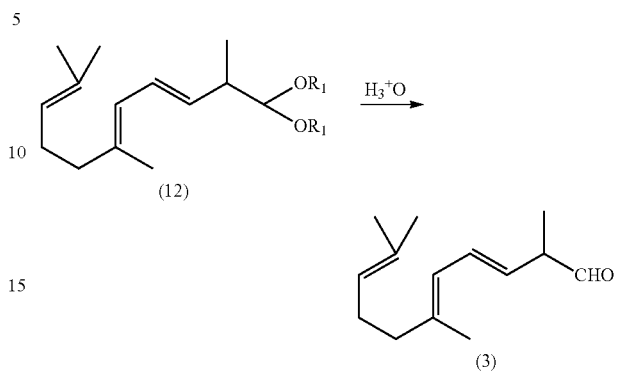

The purpose of the present invention is achieved, in the cases of overcoming limited reaction conditions of preparing lycopene as well as deficiencies of expensive iodomethane and contaminated dimethyl sulfide and dangerous DMSO sodium of preparing intermediates of lycopene, 2,6,10-trimethyl-3,5,9-undecatrienyl-1-aldehyde of formula (3).

The present inventors found two new lycopene intermediates such as 4-methyl-5,5-dialkoxy-1-pentenyl-1-phosphoric acid dialkyl ester and 2,6,10-trimethyl-1,1-dialkoxy-3,5,9-undecantriene to obtain a method of preparing 2,6,10-trimethyl-3,5,9-undecatrienyl-1-aldehyde of formula (3) by using the above-mentioned two intermediates in the course of researching.

The method of preparing 2,6,10-trimethyl-3,5,9-undecatrienyl-1-aldehyde of formula (3) comprises the following three steps:

Step (1): 3-methyl-4,4-dialkoxy-1-aldehyde of formula (11) undergoes a Wittig-Horner condensation reaction with tetra-alkyl methylene diphosphonate to produce 4-methyl-5,5-dialkoxy-1-pentenyl-1-phosphoric acid dialkyl ester of formula (10). Preferably, the step (1) comprises tetra-alkyl methylene diphosphonate reacting with bases to produce a corresponding carbanion, and then undergoing a Wittig-Horner condensation reaction with 3-methyl-4,4-dialkoxy-1-aldehyde of formula (11). It would be advantageous for fully rearrangement and dissociation of tetra-alkyl methylene diphosphonate to produce a carbanion, and it also would be better to control the Wittig-Horner condensation reaction. Besides tetra-alkyl methylene diphosphonate optionally mixes with 3-methyl-4,4-dialkoxy-1-aldehyde of formula (11), and then slowly drops it into bases. Wherein the tetra-alkyl methylene diphosphonate is tetramethyl methylene diphosphonate, tetraethyl methylene diphosphonate, or tetraisopropyl methylene diphosphonate.

The reaction sequence of the step (1) is described as follows:

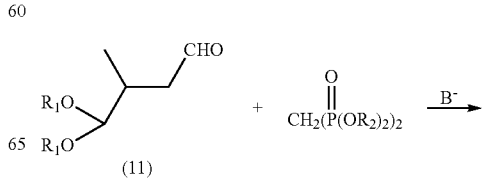

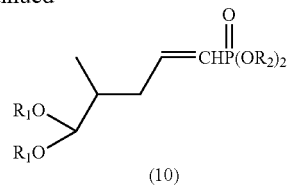

(10)

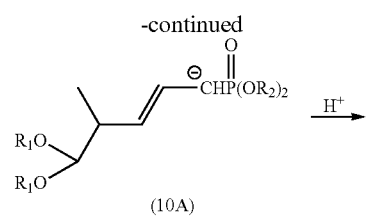

(10A)

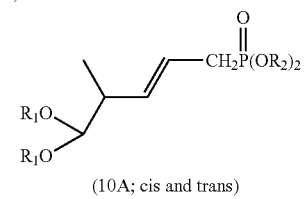

(10A; cis and trans)

The Wittig-Horner condensation reaction undergoes in the presence of bases, and no special limit of alkali is in the step. Preferably, the bases is alkali metal hydride such as sodium hydride or potassium hydride, the alkali metal salt of alcohols such as sodium ethoxide, sodium tert-butoxide or potassium tert-butoxide; the alkyl lithium such as butyl lithium. Wherein a molar ratio of dosage of 3-methyl-4,4-dialkoxy-1-aldehyde of formula (11) to the bases is 1:1.0~1.2, preferably, 1:1.02~1.1. A molar ratio of dosage of 3-methyl-4,4-dialkoxy-1-aldehyde of formula (11) to tetra-alkyl methylene diphosphonate is 1:1.05~1.15.

The Wittig-Horner condensation reaction is undergone at temperature of 0~30° C. in ether solvent or dipolar aprotic solvent. Preferably the ether solvent is ether, tetrahydrofuran or ethylene glycol dimethyl ether; the dipolar aprotic solvent is dimethyl formamide, dimethyl sulfoxide or hexamethyl phosphoric triamide. The Wittig-Horner condensation reaction proceeds at temperature of 10~20.

Step (2): 4-methyl-5,5-dialkoxy-1-pentenyl-1-phosphoric acid dialkyl ester of formula (10) undergoes a rearrangement reaction with 6-methyl-5-heptene-2-one of formula (13) to produce 2,6,10-trimethyl-1,1-dialkoxy-3,5,9-undecan-triene of formula (12). Preferably 4-methyl-5,5-dialkoxy-1-pentenyl-1-phosphoric acid dialkyl ester of formula (10) undergoes a rearrangement reaction with the bases to produce a corresponding carbanion, and adds 6-methyl-5-heptene-2-one of formula (13) undergoes a Wittig-Horner condensation reaction. It would be advantageous for fully rearrangement and dissociation of 4-methyl-5,5-dialkoxy-1-pentenyl-1-phosphoric acid dialkyl ester of formula (10) to produce a carbanion of formula (10A), and it also would be better to control the Wittig-Horner condensation reaction. The step (2) is subdivided into the following two steps:

Step (2-1): 4-methyl-5,5-dialkoxy-1-pentenyl-1-phosphoric acid dialkyl ester of formula (10) undergoes a rearrangement and dissociation reaction at temperature of –40~30° C. and in ether solvent or dipolar aprotic solvent and under protection of inert gas and in the presence of bases to produce a rearrangement product with a carbanion of formula (10A). It is found by tracking gas chromatography that 4-methyl-5,5-dialkoxy-1-pentenyl-1-phosphoric acid dialkyl ester of formula (10) fully rearranges to a carbanion of formula (10A) if providing proton to formula (10A). The rearrangement product is double bond, cis-trans isomers. The reaction sequence of the step is described as follows:

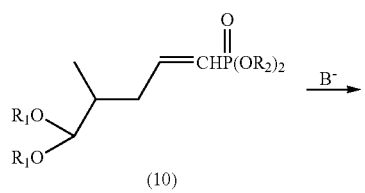

(10)

Step (2-2): after fully rearrangement reaction and dissociation, adding 6-methyl-5-heptene-2-one of formula (13) and undergoing a Wittig-Horner condensation reaction to produce 2,6,10-trimethyl-1,1-dialkoxy-3,5,9-undecan-triene of formula (12), at temperature of –40~30° C. in ether solvent or dipolar aprotic solvent and in the presence of bases. It is essentially a condensation reaction between the carbanion of formula (10A) and 6-methyl-5-heptene-2-one of formula (13), wherein the by-product is phosphonic acid dialkyl ester salt. The reaction sequence of the step is described as follows:

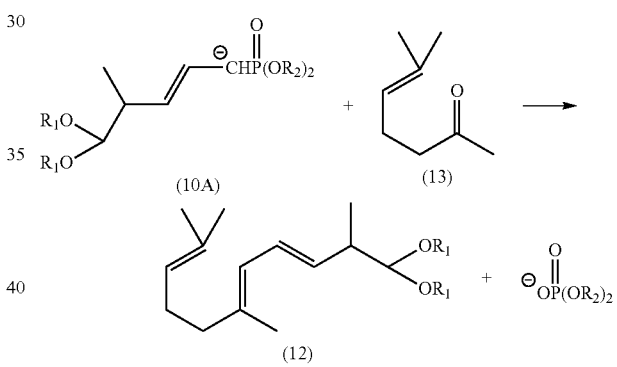

In Step (2), a molar ratio of dosage of 4-methyl-5,5-dialkoxy-1-pentenyl-1-phosphoric acid dialkyl ester of formula (10) to the bases is 1:1.0~1.2, preferably, 1:1.02~1.1. A molar ratio of dosage of 4-methyl-5,5-dialkoxy-1-pentenyl-1-phosphoric acid dialkyl ester of formula (10) to 6-methyl-5-heptene-2-one of formula (13) is 1:0.8~1.2, preferably 1:0.9~1.1.

The reactions of Step (2-1) and Step (2-2) are undergone under bases. Preferably the bases is alkali metal hydride such as sodium hydride or potassium hydride, the alkali metal salt of alcohols such as sodium ethoxide, sodium tert-butoxide or potassium tert-butoxide; the alkyl lithium such as butyl lithium. In Step (2-1) and Step (2-2), the ether solvent is ether, tetrahydrofuran or ethylene glycol dimethyl ether; the dipolar aprotic solvent is dimethyl formamide, dimethyl sulfoxide or hexamethyl phosphoric triamide. The preferred reaction temperature is –20~10° C.

After finishing the condensation reaction, water is added to segregate from organic solvent, the by-product such as phosphoric acid diethyl ester is dissolved in water, the product of 2,6,10-trimethyl-1,1-dialkoxy-3,5,9-undecantriene of formula (12) is in organic phase, to obtain the objective product of 2,6,10-trimethyl-1,1-dialkoxy-3,5,9-undecantriene of formula (12) after evaporation to remove the solvent.

Step (3): 2,6,10-trimethyl-1,1-dialkoxy-3,5,9-undecan-triene of formula (12) is hydrolyzed to produce the objective product of 2,6,10-trimethyl-3,5,9-undecatrienyl-1-aldehyde of formula (3). In particular, the hydrolysis reaction of 2,6,10-trimethyl-1,1-dialkoxy-3,5,9-undecan-triene of formula (12) is undergone in the presence of acid catalyst, water and homogeneous solvent. The acid catalyst is sulfuric acid, p-toluene sulfonic acid, trifluoroacetic acid, amino sulfonic acid, etc. No limit is in the hydrolysis reaction. The homogeneous solvent is tetrahydrofuran, acetone. A weight ratio of dosage of 2,6,10-trimethyl-1,1-dialkoxy-3,5,9-undecan-triene of formula (12) to the acid catalyst is 1:0.04-0.1. A ratio of dosage of 2,6,10-trimethyl-1,1-dialkoxy-3,5,9-undecan-triene of formula (12) to the homogeneous solvent is 1:5-10 (W/V). A weight ratio of dosage of 2,6,10-trimethyl-1,1-dialkoxy-3,5,9-undecan-triene of formula (12) to water is 1:0.8~3.2. The hydrolysis reaction is undergone at the temperature of 10~35° C. under tracking gas chromatography.

The reaction sequence of preparing 2,6,10-trimethyl-3,5,9-undecatrienyl-1-aldehyde of formula (3) is described as follows:

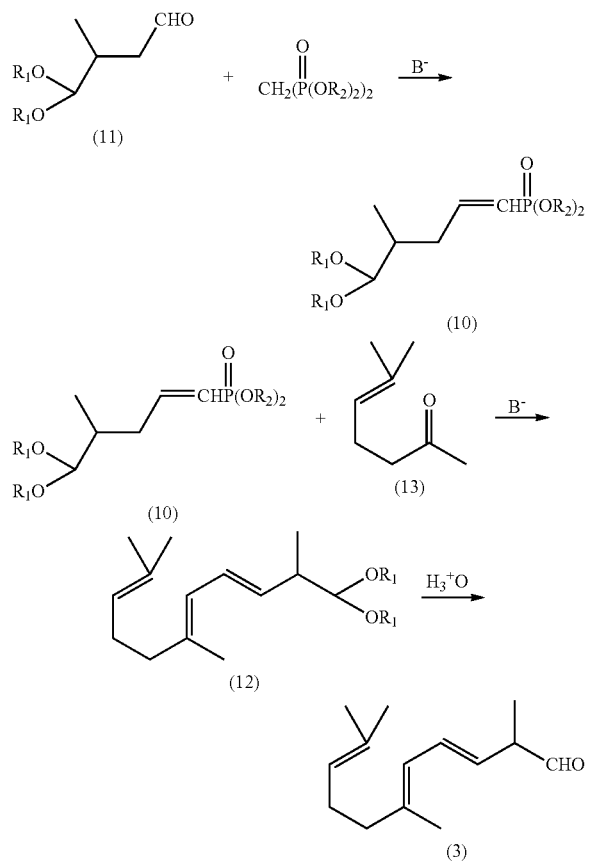

All of these reactions are undergone under the protection of inert gas such as nitrogen, argon or any other one or more inert gas.

After finishing the hydrolysis reaction of Step (3), sodium bicarbonate solution is added into the reaction system to neutralize until neutral, and then remove the solvent by evaporation at reduced pressure, subsequently add water-immiscible organic solvent such as methylene chloride, cyclohexane, etc thereinto to extract. After stratification, the organic layer is evaporated to dryness to produce crude product of 2,6,10-trimethyl-3,5,9-undecatrienyl-1-aldehyde of formula (3). The crude product is refined by rectification to obtain pure product of 2,6,10-trimethyl-3,5,9-undecatrienyl-1-aldehyde of formula (3).

In the method of preparing 2,6,10-trimethyl-3,5,9-undecatrienyl-1-aldehyde of formula (3), the reaction raw materials such as 3-methyl-4,4-dialkoxy-1-aldehyde of formula (11), tetra-alkyl methylene diphosphonate and 6-methyl-5-heptene-2-one of formula (13) are provided by Zhejiang Medicine Co., Ltd Xinchang Pharmaceutical Factory. Besides, these compounds may also be prepared by reference documents, for example, 3-methyl-4,4-dialkoxy-1-aldehyde of formula (11) may be prepared according to the method disclosed in U.S. Pat. No. 4,675,451. The reaction sequence is described as follows:

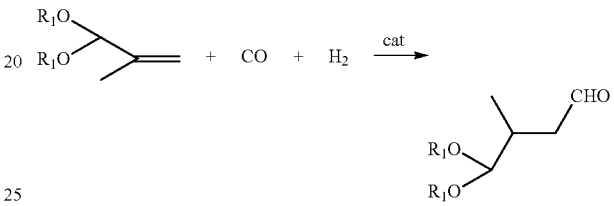

Both of tetra-alkyl methylene diphosphonate and 6-methyl-5-heptene-2-one of formula (13) are obtained from regular industrial raw materials.

As described above, it takes three steps for the present invention to produce the key intermediate of lycopene, 2,6,10-trimethyl-3,5,9-undecatrienyl-1-aldehyde of formula (3) by using 3-methyl-4,4-dialkoxy-1-aldehyde of formula (11) as raw materials. Hence it takes the advantages of short process route, easy acquisition of raw materials, low cost and high industrial value.

The method of preparing lycopene is also adopted based on the method of the Chinese application No. 2010101042817.

Step (1): 2,6,10-trimethyl-3,5,9-undecatrienyl-1-aldehyde of formula (3) undergoes a Wittig-Horner condensation reaction with tetra-alkyl methylene diphosphonate, at temperature of 0~30° C. in ether solvent or dipolar aprotic solvent and under protection of inert gases in the presence of bases, to produce 1,4,6,10-tetra-double bond pentadec-carbon phosphonate of formula (4). The reaction sequence is described as follows.

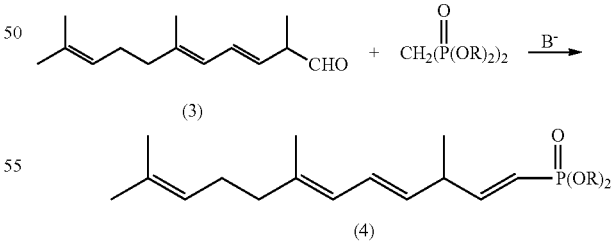

wherein $R_1$ and $R_2$ are $C_{1-4}$ alkyl.

Step (2): 1,4,6,10-tetra-double bond pentadec-carbon phosphonate of formula (4) undergoes a rearrangement reaction at temperature of −40~30° C. and in ether solvent or dipolar aprotic solvent and under protection of inert gas and in the presence of alkali; and then decyl di-aldehyde of formula (8) is added to undergo a Wittig-Horner condensation reaction to produce lycopene of formula (1) at temperature of −40~30° C. in ether solvent or dipolar aprotic solvent and under protection of inert gas in the presence of bases. The reaction sequence is described as follows.

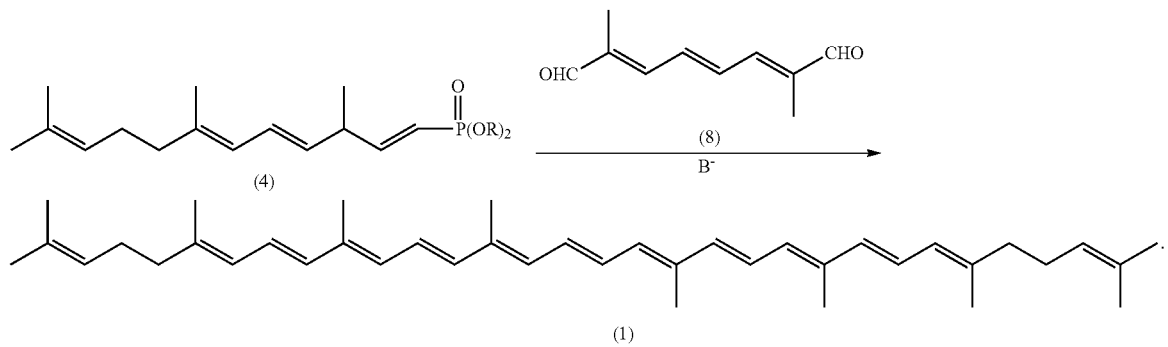

As described above, it takes five steps for the present invention to produce the objective product of lycopene (1) by using 3-methyl-4,4-dialkoxy-1-aldehyde of formula (11) as raw materials. Hence it takes the advantages of short process route, easy acquisition of raw materials, low cost and high industrial value.

Please note that the intermediate of 4-methyl-5,5-dialkoxy-1-pentenyl-1-phosphoric acid dialkyl ester of formula (10) is a single compound verified by tracking gas chromatography and nuclear magnetic resonance. The condensation product of 2,6,10-trimethyl-1,1-dialkoxy-3,5,9-undecantriene of formula (12), the hydrolysate of 2,6,10-trimethyl-3,5,9-undecatrienyl-1-aldehyde of formula (3), and 1,4,6,10-tetra-double bond pentadec-carbon phosphonate of formula (4) are cis-trans isomeric mixtures. But these cis-isomers of these intermediates do not affect the all-trans structure of the final product-lycopene of formula (1), because the final product of all-trans lycopene are obtained through cis-trans isomerization and purification of the crude product of lycopene

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Apparatuses and devices of Examples of the present invention are as follows: Gas chromatograph-Mass Spectrometer, MS5973N-GC6890N (Agilent Technologies, US); Nuclear Magnetic Resonance Spectrometer, AVANCE DMX II I 400M (TMS as internal standard, Bruker Corporation); infrared spectrometer, NICOLET 360FT-IR; gas chromatograph, Techcomp Corp. 7890F.

Example 1

Preparation of 4-methyl-5,5-dimethoxy-1-pentenyl-1-phosphoric acid diethyl ester of formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 34.5 g of tetraethyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10~15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 26.2 g crude product of 4-methyl-5,5-dimethoxy-1-pentenyl-1-phosphoric acid diethyl ester with colorless liquid, content of the crude product is 92.2% detected by GC analysis, yield is 86.9%. The crude product is evaporated with a boiling point of 107-111° C./1 mmHg Determination of Product Structure:

GC-MS (m/e): 279, 265, 249, 220, 205, 195, 177, 163, 149, 121, 111, 95, 81, 75 (100%), 67, 47, 29;

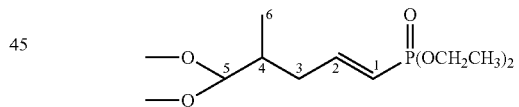

$^1$HNMR (δ, ppm, 400 MHz, CDCl$_3$): 0.920 (d, J=6.8 Hz, 3H, C6-H); 1.327 (t, J=7.2 Hz, 6H, OCH$_2$C*H$_3$); 1.907-1.972 (m, 1H, C4-H); 2.025-2.103, 2.426-2.488 (m, m, 2H, C3-H); 3.339, 3.355 (s, s, 6H, (OCH$_3$)$_2$); 4.038-4.109 (m, 4H, OC*H$_2$CH$_3$); 4.054 (d, J=6.4 Hz, 1H, C5-H); 5.674 (dd, J=16.8 Hz, 21.6 Hz, 1H, C1-H); 6.696-6.793 (m, 1H, C2-H);

$^{13}$CNMR (δ, ppm, 400 MHz, CDCl$_3$): 152.12, 152.07 (C2); 119.40, 117.54 (C1); 108.11 (C5); 61.63, 61.58 (POC*H$_2$CH$_3$); 54.60, 54.01 (OCH$_3$); 36.84, 36.62 (C3); 35.23 (C4); 16.42, 16.35 (OCH$_2$C*H$_3$); 14.45 (C6).

Example 2

Preparation of 4-methyl-5,5-dimethoxy-1-pentenyl-1-phosphoric acid dimethyl ester of formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 27.9 g of tetramethyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10~15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 25.2 g crude product of 4-methyl-5,5-dimethoxy-1-pentenyl-1-phosphoric acid dimethyl ester of formula (10), with colorless liquid, content of the crude product is 91.7% detected by GC analysis, yield is 91%.

Determination of Product Structure:

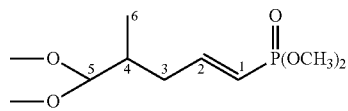

$^1$HNMR (δ, ppm, 400 MHz, CDCl3): 0.923 (d, J=6.8 Hz, 3H, C6-H); 1.897-1.962 (m, 1H, C4-H); 2.038-2.116, 2.417-2.523 (m, m, 2H, C3-H); 3.356, 3.367 (s, s, 6H, (OCH3)2); 3.709, 3.736 (m, 6H, OC*H3); 4.057 (d, J=6.0 Hz, 1H, C5-H); 5.647 (dd, J=16.8 Hz, 21.6 Hz, 1H, C1-H); 6.715-6.847 (m, 1H, C2-H);

13CNMR (δ, ppm, 400 MHz, CDCl3): 153.27, 153.22 (C2); 117.83, 115.97 (C1); 108.02 (C5); 54.59, 53.98 (OCH3); 52.28, 52.23 (POCH3); 36.87, 36.65 (C3); 35.14 (C4); 14.45 (C6).

Example 3

Preparation of
4-methyl-5,5-dimethoxy-1-pentenyl-1-phosphoric acid diisopropyl ester of formula (10)

4.4 g of sodium hydride (0.11 mol) (60% content) is added in a 250 ml three necked flask under protection of nitrogen, and washed with 20 ml of hexane for twice to remove paraffin oil from sodium hydride, and then 20 ml of toluene is added into the flask, and then 60 ml of toluene dissolving 41.3 g of tetraisopropyl methylene diphosphonate (0.12 mol) is dropped into the flask under magnetic stirring at temperature 10~15° C. of cold water bath for half an hour to release a large amount of gas, and continuously stirring for half an hour.

Then 40 ml of toluene dissolving 14.4 g of 3-methyl-4,4-dimethoxy-1-aldehyde of formula (11) (0.1 mol) is dropped into the flask at temperature kept at 10~15° C. of cold water bath for half an hour, and continuously stirring for half an hour to form a mixture.

40 ml of water is added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain 29.3 g crude product of 4-methyl-5,5-dimethoxy-1-pentenyl-1-phosphoric acid diisopropyl ester, with colorless liquid, content of the crude product is 92.5% detected by GC analysis, yield is 89.7%.

Determination of Product Structure:

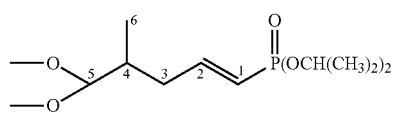

$^1$HNMR (δ, ppm, 400 MHz, CDCl$_3$): 0.914 (d, J=6.4 Hz, 3H, C6-H); 1.327-1.365 (m, 12H, OCH(C*H$_3$)$_2$); 1.903-1.986 (m, 1H, C4-H); 2.025-2.082, 2.325-2.456 (m, m, 2H, C3-H); 1.608, 3.363, 3.354 (s, s, s, 6H, (OCH$_3$)$_2$); 4.055 (d, J=6.0 Hz, 1H, C5-H); 4.735-4.814 (m, 2H, OC*H(CH$_3$)$_2$); 5.682 (dd, J=17.2 Hz, 20.8 Hz, 1H, C1-H); 6.645-6.734 (m, 1H, C2-H);

$^{13}$CNMR (δ, ppm, 400 MHz, CDCl$_3$): 150.85, 150.80 (C2); 121.01, 119.15 (C1); 108.00 (C5); 71.14, 71.11, 71.08 (OC*H(CH$_3$)$_2$); 54.48, 53.93 (OCH$_3$); 36.70, 36.47 (C3); 35.15 (C4); 23.91, 23.95, 24.02, 24.06 (OCH(C*H$_3$)$_2$); 14.34 (C6).

Example 4~10

Preparation of
4-methyl-5,5-dimethoxy-1-pentenyl-1-phosphoric acid diethyl ester of formula (10) by a condensation reaction in conditions of different alkali, different solvent and different temperature Using the same method as Example 1, a certain amount of alkali and solvent (refer to Table 1) are added into a 250 ml three necked flask under protection of nitrogen, and 40 ml solvent (refer to solvent of Table 1) dissolving a certain amount of tetraethyl methylene diphosphonate (refer to molar weight of Table 1) is dropped into the flask under magnetic stirring at temperature 10~15° C. of cold water bath for half an hour, and continuously stirring for 20 minutes.

Then 20 ml solvent (refer to solvent of Table 1) dissolving 5.8 g of 3-methyl-4,4-dimethoxy-1-aldehyde of formula (11) (0.040 mol) is dropped into the flask at temperature kept at certain temperature (refer to temperature of Table 1) for half an hour, and continuously stirring for 20 minutes to form a mixture.

40 ml of water and 100 ml ether are added into the mixture under stirring for 10 minutes until stratification, and the organic layer is separated from it after stratification. The organic layer is washed with 40 ml of 10% sodium chloride aqueous solution, and dried with magnesium sulfate and subsequently filtered, and then solvent is removed via reduced pressure evaporation to obtain crude product of 4-methyl-5, 5-dimethoxy-1-pentenyl-1-phosphoric acid diethyl ester of formula (10) with colorless or faint yellow liquid, content of the crude product is detected by GC analysis and yield is measured. Results are shown in Table 1.

TABLE 1

Results of Reactants, Reaction Temperatures of Condensation Reaction of Examples 4~10

| Example | Alkali | Amount of alkali (mole) | Solvent | Tetraethyl methylene diphosphonate (mole) | Reaction temperature (° C.) | Amount of Product (g) | GC content (%) | Yield (%) |
|---|---|---|---|---|---|---|---|---|
| 4 | sodium ethoxide | 0.0480 | toluene | 0.0520 | 5 | 10.4 | 93.2 | 87.2 |
| 5 | sodium tert-butoxide | 0.0400 | ethylene glycol dimethyl ether | 0.0400 | 10 | 10.8 | 92.9 | 89.6 |
| 6 | potassium tert-butoxide | 0.0408 | dimethyl formamide | 0.0420 | 20 | 11.2 | 93.1 | 93.8 |
| 7 | n-butyl lithium | 0.0480 | tetrahydrofuran/ n-hexane | 0.0520 | 0 | 11.2 | 93.5 | 94.2 |
| 8 | DMSO sodium salt | 0.0420 | DMSO | 0.0432 | 30 | 10.0 | 91.3 | 82.1 |
| 9 | potassium hydride | 0.0412 | toluene | 0.0432 | 20 | 11.2 | 92.5 | 93.2 |
| 10 | soduim methoxide | 0.0440 | ether | 0.0460 | 15 | 8.4 | 89.7 | 73.3 |

Note:
n-butyl lithium is 2.5 mol/l n-hexane solution thereof
Finally combine these crude products obtained to get 73.2 g crude product of 4-methyl-5,5-dimethoxy-1-pentenyl-1-phosphoric acid diethyl ester of formula (10) used for the following condensation reaction.

Example 11

Preparation of 2,6,10-trimethyl-1,1-dimethoxy-3,5,9-undecantriene of formula (12)

6.2 g (0.11 mol) of potassium tert-butoxide and 30 ml mixture of tetrahydrofuran: dimethyl sulfoxide (8:1 (v:v)) are added in a 250 ml a three neck flask in cold water bath under mechanical stirring, under protection of nitrogen, 14.0 g (0.05 mole) of 4-methyl-5,5-dimethoxy-1-pentenyl-1-phosphoric acid diethyl ester of formula (10) is dropped into the flask at temperature of −30~−25° C. for half an hour until the end of dropping, continuously stirring under the same temperature for an hour to make a carbanion undergo a dissociative reaction fully. At this time the samples are took and a small amount of water is added into the samples for stratification, the organic layer is detected by gas chromatography analysis to confirm 4-methyl-5,5-dimethoxy-1-pentenyl-1-phosphoric acid diethyl ester of formula (10) are fully rearranged to 4-methyl-5,5-dimethoxy-2-pentenyl-1-phosphoric acid diethyl ester of formula (10A), the rearrangement product is a mixture of cis-trans isomers. The reaction sequence of the stet is described as follows:

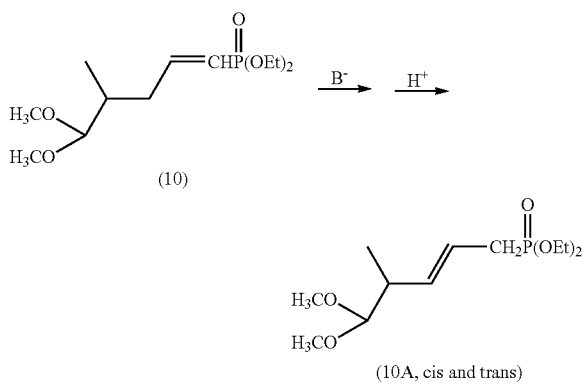

Determination of Product Structure:
GC-MS (m/e): 279, 262, 247, 231, 223, 191, 163, 135, 125, 109, 102, 93, 81, 75 (100%), 47, 29;

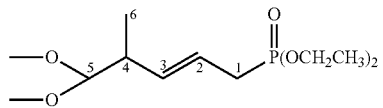

$^1$HNMR (δ, ppm, 400 MHz, CDCl$_3$): 0.878-0.967, 0.984-1.046 (m, m, 3H, C6-H); 1.319 (s, 6H, OCH$_2$C*H$_3$); 1.704-1.750, 1.894-1.956 (m, m, 2H, C$_1$—H); 2.450-2.604 (m, 1H, C4-H); 3.356 (s, 6H, (OCH$_3$)$_2$); 4.001-4.203 (m, 4H, OC*H$_2$CH$_3$); 4.016-4.145 (m, 1H, C5-H); 5.367-5.506 (m, 1H, C2-H); 5.582-5.707 (m, 1H, C3-H)
$^{13}$CNMR (δ, ppm, 400 MHz, CDCl$_3$): 136.42, 136.28 (C3); 119.26, 119.15 (C2); 107.98, 107.82 (C5); 61.27, 61.23 (POC*H$_2$CH$_3$); 53.76, 53.73 (OCH$_3$); 33.59 (C4); 31.25, 30.95 (C1); 16.39 (OCH$_2$C*H$_3$); 14.92, 14.72 (C6).

Then, 6.3 g of 6-methyl-5-heptene-2-one of formula (13) (0.05 mol) is dropped into the flask at a temperature of −30~−25° C. for an hour, continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residual material is evaporated at reduced pressure, the fraction within 99-103° C./1 mmHg is collected 9.4 g, the fraction is a colorless transparent liquid, the product shows four peaks through GC analysis, the total content is 87.5%, the yield is 65.3%. Four products are respectively 3,4- double bond cis-trans isomers and 5,6- double bond cis-trans isomers.

Verification of Structure of the Product: (Only all Trans Isomers are Listed, Other Cis Isomers are Omitted):
GC-MS (m/e): 252, 220, 192 (100%), 178, 165, 152, 115, 102, 91, 77, 65, 51, 39;

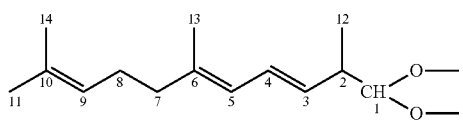 [SMILES: COC(OC)C(C)/C=C/C=C(\C)CCC=C(C)C]

$^1$HNMR (δppm, 400 MHz, CDCl$_3$): 1.003 (d, J=6.8 Hz, 3H, C$_{12}$—H); 1.605 (s, 3H, C$_{14}$—H); 1.679 (s, 3H, C$_{11}$—H); 1.745 (s, 3H, C$_{13}$—H); 2.036-2.184 (m, 4H, C$_7$—H, C$_8$—H); 2.928-2.969 (m, 2H, C$_2$—H); 3.378, 3.381 (s, s, 6H, (OCH$_3$)$_2$); 4.120-4.144 (m, 1H, C$_1$—H); 5.099-5.130 (m, 1H, C$_9$—H); 5.190-5.268 (q, J=10.4 Hz, 1H, C$_3$—H); 6.058 (d, J=11.2 Hz, 1H, C$_5$—H); 6.188-6.253 (m, 1H, C$_4$—H)

$^{13}$CNMR (δppm, 400 MHz, CDCl$_3$): 139.44 (C6); 131.61 (C10); 130.07 (C3); 124.87 (C4); 124.05 (C9); 119.76 (C5); 108.15 (C1); 53.64 (OCH$_3$); 40.29 (C7); 35.27 (C2); 26.57 (C8); 25.70 (C11); 17.68 (C12); 16.52 (C14); 16.16 (C13);

DEPT135: 139.44; 131.61; 130.07; 124.87; 124.05; 119.76; 108.15; 53.64; 40.29 (D); 35.27; 26.57 (D); 25.70; 17.68; 16.52; 16.16.

Example 12

Preparation of 2,6,10-trimethyl-1,1-dimethoxy-3,5,9-undecantriene of formula (12)

6.2 g of potassium tert-butoxide (0.11 mol) and 30 ml mixture of tetrahydrofuran: dimethyl sulfoxide (8:1 (v:v)) are added into a 250 ml a three neck flask in cold water bath under mechanical stirring, under protection of nitrogen, 12.7 g (0.05 mole) of 4-methyl-5,5-dimethoxy-1-pentenyl-1-phosphoric acid dimethyl ester of formula (10) is dropped into the flask at temperature of −30~−25° C. for half an hour, and then continuously stirring under the same temperature for an hour to make a carbanion undergo dissociative reaction fully.

Then, 6.3 g (0.05 mol) of 6-methyl-5-heptene-2-one of formula (13) is dropped into the flask at a temperature of −30~−25° C. for an hour, and continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residue is evaporated at reduced pressure, the fraction within 99-103° C./1 mmHg is collected 9.4 g, the fraction is a colorless transparent liquid, the product shows four peaks through GC analysis, the total content is 86.7%, the yield is 66.1%. Four products are respectively 3,4-double bond cis-trans isomers and 5,6- double bond cis-trans isomers. Datum of $^1$HNMR of example 12 is the same as that of Example 11.

Example 13

Preparation of 2,6,10-trimethyl-1,1-dimethoxy-3,5,9-undecantriene of formula (12)

6.2 g of potassium tert-butoxide (0.11 mol) and 30 ml mixture of tetrahydrofuran: dimethyl sulfoxide (8:1 (v:v)) are added into a 250 ml a three neck flask in cold water bath under mechanical stirring, under protection of nitrogen, 15.1 g (0.05 mole) of 4-methyl-5,5-dimethoxy-1-pentenyl-1-phosphoric acid diisopropyl ester of formula (10) is dropped into the flask at temperature of −30~−25° C. for half an hour, and then continuously stirring under the same temperature for an hour to make a carbanion undergo dissociative reaction fully.

Then, 6.3 g (0.05 mol) of 6-methyl-5-heptene-2-one of formula (13) is dropped into the flask at a temperature of −30~−25° C. for an hour, and continuously stirring for half an hour at the same temperature, and trace the end of the reaction by tracking gas chromatography. 30 ml of water and 60 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residue is evaporated at reduced pressure, the fraction within 99-103° C./1 mmHg is collected 10.1 g, the fraction is a colorless transparent liquid, the product shows four peaks through GC analysis, the total content is 87.8%, the yield is 70.4%. Four products are respectively 3,4-double bond cis-trans isomers and 5,6- double bond cis-trans isomers. Datum of $^1$HNMR of example 12 is the same as that of Example 11.

Examples 14-19

Preparation of 2,6,10-trimethyl-1,1-dimethoxy-3,5,9-undecantriene of formula (12) in different conditions The crude product of 73.2 g of 4-methyl-5,5-dimethoxy-1-pentenyl-1-phosphoric acid diethyl ester of formula (10) of Examples 4-10 and 12.0 g of the residual crude product of Example 1 are combined together to obtain crude products, the total amount is 85.2 g, the total content is 92.7%, the crude products is used for the following experiment.

Using the same the method as Example 11, a certain amount of alkali and 20 ml solvent (refer to Table 2) are added into a 250 ml a three necked flask under protection of nitrogen, and 20 ml solvent (refer to solvent of Table 2) dissolving a certain amount of 4-methyl-5,5-dimethoxy-1-pentenyl-1-phosphoric acid diethyl ester of formula (10) (refer to molar weight of Table 2) is dropped into the flask under magnetic stirring at a certain temperature (refer to temperature of Table 2) for half an hour, and continuously stirring for an hour to make a carbanion undergo dissociative reaction.

Then a solvent (refer to solvents of Table 2) dissolving 6.3 g of 6-methyl-5-heptene-2-one of formula (13) (0.05 mol, cis-trans isomers mixture) is dropped into the flask at a certain temperature for an hour, continuously stirring for half an hour at the same temperature, and determine the end of the reaction by tracking gas chromatography. 30 ml of water and 50 ml of ether are added under stirring for 10 minutes, and then wash the ether layer with 5% sodium chloride aqueous solution for 3 times (15 ml each time) after stratification, the organic layer is dried over magnesium sulfate, and subsequently filtered, the filtrate is removed via reduced pressure evaporation to obtain a crude product, the residual material is evaporated at reduced pressure, the fraction within 97-101° C./1 mmHg is collected for measuring content of the crude product by GC analysis and yield. Results are shown in Table 2.

TABLE 2

Reactants, Reaction Temperatures And Reaction Results of The of Examples 14-19

| examples | alkali | amount of alkali (mol) | solvent | 4-methyl-5,5-dimethoxy-1-pentenyl-1-phosphoric acid diethyl ester (g, mole) | reaction temperature (° C.) | amount of Product (g) | GC content (%) | yield (%) |
|---|---|---|---|---|---|---|---|---|
| 14 | sodium ethoxide | 0.06 | toluene | 13.9, 0.050 | 30 | 6.3 | 86.2 | 43.1 |
| 15 | sodium tert-butoxide | 0.05 | glycol dimethyl ether | 12.5, 0.045 | −10 | 8.2 | 87.5 | 56.9 |
| 16 | n-butyl lithium | 0.051 | tetrahydrofuran/n-hexane | 13.0, 0.047 | −40 | 9.8 | 91.6 | 71.2 |
| 17 | potassium tert-butoxide | 0.063 | dimethyl sulfoxide | 17.4, 0.063 | −20 | 8.9 | 90.7 | 64.1 |
| 18 | potassium tert-butoxide | 0.0567 | hexamethyl-phosphoric triamide | 15.6, 0.056 | 10 | 8.9 | 91.4 | 64.5 |
| 19 | potassium tert-butoxide | 0.046 | hexamethyl-phosphoric triamide | 11.6, 0.042 | 0 | 8.9 | 89.3 | 62.4 |

Note:
n-butyl lithium is 2.5 mol/l n-hexane solution thereof
Finally combine these crude products to obtain 51 g crude product of 2,6,10-trimethyl-1,1-dimethoxy-3,5,9-undecantriene of formula (12) together with 80.2 g crude product of 2,6,10-trimethyl-1,1-dimethoxy-3,5,9-undecantriene of formula (12) of Examples 11,12,13 used for the following condensation reaction.tests, wherein their datum of $^1$HNMR of Examples 14~19 are the same as that of Example 11.

Example 20

Preparation of 2,6,10-trimethyl-3,5,9-undecatrienyl-1-aldehyde of formula (3)

12.6 g of 2,6,10-trimethyl-1,1-dimethoxy-3,5,9-undecantriene of formula (12) prepared above (0.05 mol), 100 ml of tetrahydrofuran solvent and 1.2 g of p-toluene sulfonic acid are added into a 250 ml three neck flask under protection of nitrogen, 22 g of water is dropped, and stirred for one day at a temperature of 20~25° C. after mixing, and traced the end of the reaction by tracking gas chromatography, and neutralized with 2 g of sodium bicarbonate and 20 ml of water, tetrahydrofuran is evaporated by water pump under reduced pressure, then 100 ml of cyclohexane is added, the organic layer is separated after stratification, and then the organic layer is washed with 30 ml of water, dried over anhydrous magnesium sulfate and subsequently solvent is recovered at reduced pressure to obtain 10.5 g of crude product of 2,6,10-trimethyl-3,5,9-undecatrienyl-1-aldehyde of formula (3), a mixture comprising 3-cis-trans, 5-cis-trans isomers and other various isomers, the total content of the product is 85.1% detected by GC analysis and the yield is 86.8%.

Determination of Product Structure:

GC-MS (m/e): 206, 191, 163, 135, 121, 109, 95 (100%), 69, 55, 41;

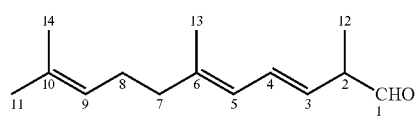

$^1$HNMR (δppm, 400 MHz, CDCl$_3$): 1.189-1.206 (m, 3H, C$_{12}$—H), 1.427 (s, 3H, C$_{14}$—H), 1.610 (s, 3H, C$_{11}$—H), 1.687 (s, 3H, C$_{13}$—H), 1.746-1.869 (m, 2H, C$_8$—H), 2.092-2.134 (m, 2H, C$_7$—H), 3.455-3.563 (m, 1H, C$_2$—H), 5.092-5.101 (m, 1H, C$_9$—H), 5.095-5.164 (m, 1H, C$_3$—H), 6.058 (d, J=9.6 Hz, 1H, C$_5$—H), 6.445 (t, J=9.6 Hz, 1H, C$_4$—H), 9.537 (s, 1H, —CHO);

$^{13}$CNMR (400 MHz, CDCl$_3$) δ(ppm): 201.03 (C1); 142.10 (C6); 128.56 (C4); 124.04 (C3); 123.75 (C9); 123.60 (C10); 119.34 (C5); 45.92 (C2); 40.27 (C7); 26.90 (C8); 25.66 (C11); 17.69 (C14); 16.67 (C13); 14.04 (C12);

DEPT135: 201.03; 128.56; 124.04; 123.75; 119.34; 45.92; 40.27 (D); 26.90 (D); 25.66; 17.69; 16.67; 14.04;

Examples 21-27

Preparation of 2,6,10-trimethyl-3,5,9-undecatrienyl-1-aldehyde of formula (3) in different conditions 6.3 g (0.025 mol) of 2,6,10-trimethyl-1,1-dimethoxy-3,5,9-undecatrienyl-1-aldehyde of formula (12), a certain amount of homogeneous solvent and certain acid catalyst (refer to amounts of Table 3) are added into a 100 ml three neck flask under protection of nitrogen. A certain amount of water (refer to amounts of Table 3) is dropped after mixing and stirred at a certain temperature (refer to temperatures of Table 3). The reaction is tracked by gas chromatography till the end of the reaction, and neutralized with 1.5 g of sodium bicarbonate and 15 ml of water, solvent is evaporated by water pump under reduced pressure, and then 50 ml of cyclohexane is added, the organic layer is separated after stratification. The organic layer is washed with 20 ml of water, dried over anhydrous magnesium sulfate and subsequently solvent is recovered at reduced pressure to obtain crude product of 2,6,10-trimethyl-3,5,9-undecatrienyl-1-aldehyde of formula (3), used for measuring content of the crude product by GC analysis and yield. Results are shown in Table 3.

TABLE 3

Reactants, Reaction Temperatures and Results of Hydrolysis Reaction of Examples 21-27

| examples | kinds of acid catalyst | amount of acid catalyst (g) | homogeneous solvent and amount(ml) | amount of water (g) | reaction temperture (° C.) | amount of product (g) | GC content (%) | Yield (%) |
|---|---|---|---|---|---|---|---|---|
| 21 | sulfuric acid | 0.025 | tetrahydrofuran, 25 | 5.0 | 15 | 5.3 | 83.5 | 85.9 |
| 22 | sulfuric acid | 0.045 | acetone, 30 | 6.0 | 10 | 5.3 | 82.1 | 84.5 |
| 23 | trifluoroacetic acid | 0.055 | tetrahydrofuran, 55 | 20.0 | 20 | 5.5 | 85.3 | 91.1 |
| 24 | p-toluene sulfuric acid | 0.050 | tetrahydrofuran, 50 | 12.6 | 35 | 5.7 | 86.1 | 95.3 |
| 25 | amino sulfuric acid | 0.025 | tetrahydrofuran, 25 | 8.0 | 30 | 5.5 | 86.4 | 92.3 |
| 26 | p-toluene sulfuric acid | 0.032 | acetone, 32 | 6.3 | 35 | 5.6 | 85.1 | 92.6 |
| 27 | p-toluene sulfuric acid | 0.063 | acetone, 63 | 18.9 | 35 | 5.7 | 85.8 | 95.0 |

2,6,10-trimethyl-3,5,9-undecatrienyl-1-aldehyde of formula (3) is combined together to obtain the crude product of 38.6 g, the content is 84.1% detected by GC analysis, the total yield for seven batches of hydrolysis is 90.0%. The crude product is used in the following reaction.

Example 28

Preparation of 1,4,6,10-tetra-double bond pentadec-carbon phosphonate of formula (4) (3,7,11-trimethyl-1,4,6,10-dodecatetraenyl phosphonic acid diethyl ester)

4.4 g (0.11 mol) of sodium hydride (60% content) is added in a 250 ml three neck flask under protection of nitrogen, washed with 20 ml hexane for twice to remove paraffin oil, and then 40 ml of toluene is added, 80 ml of toluene dissolving 34.4 g tetraethyl methylene diphosphonate (0.12 mol) is dropped under magnetic stirring, at the temperature of 10-15° C. in cold water bath for half an hour, a large amount of gas is released, and continuously stirring for half an hour.

Then, 40 ml of toluene dissolving 20.6 g (0.1 mol) of 2,6,10-trimethyl-3,5,9-undecatrienyl-1-aldehyde of formula (3) is dropped at the temperature 10-15° C. of cold water bath for half an hour, and continuously stirring for half an hour.

40 ml water is added into the reaction mixture under stirring for 10 minutes, the organic layer is separated after stratification. The organic layer is washed with 40 ml of 10% sodium chloride aqueous solution, dried over magnesium sulfate and subsequently filtered, and evaporated at reduced pressure to remove solvent, and obtain 31.1 g of crude product of 1,4,6,10-tetra-double bond pentadec-carbon phosphonate of formula (4) (3,7,11-trimethyl-1,4,6,10-dodecatetraenyl phosphonic acid diethyl ester), a light yellow liquid, GC content is 93.2% and yield is 91.5%.

Determination of Product Structure:

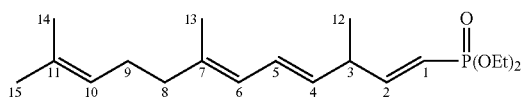

$^1$HNMR (δppm, 400 MHz, CDCl$_3$): 6.741 (t, J=19.6 Hz, 1H, C2-H), 6.242 (t, J=11.2 Hz, 1H, C5-H), 5.996 (d, J=11.6 Hz, 1H, C6-H), 5.628 (t, J=19.2 Hz, 1H, C1-H), 5.062-5.141 (m, 2H, C4-H and C10-H), 4.023-4.095 (m, 4H, O—C*H$_2$—CH$_3$), 3.43-3.53 (m, 1H, C3-H), 2.056-2.151 (m, 4H, C8-H and C9-H), 1.825 and 1.803 (s, 3H, C13-H), 1.686 (s, 3H, C14-H), 1.609 (s, 3H, C15-H), 1.313 (t, J=7.2 Hz, 6H, O—CH$_2$—C*H3), 1.154 (d, J=6.8 Hz, 3H, C12-H)

Example 29

Preparation of Lycopene 6.8 g (0.02 mol) of 1,4,6,10-tetra-double bond pentadec-carbon phosphonate of formula (4) (3,7,11-trimethyl-1,4,6,10-dodecatetraenyl phosphonic acid diethyl ester) of Example 28 and 30 ml mixture of tetrahydrofuran: dimethyl sulfoxide (8:1 (v:v)) are added into a 250 ml three neck flask under protection of nitrogen and mechanical stirring, at the temperature of 5° C. of ice water bath, 2.3 g (0.021 mol) of potassium tert-butoxide is added, continuously stirring for 2 hours under the same temperature, 10 ml of mixture of tetrahydrofuran: dimethyl sulfoxide (8:1 (v:v)) dissolving 1.6 g of C-10 dialdehyd of formula (8) (refer to Example XIV of preparation of C-10 dialdehyd (8) in U.S. Pat. No. 5,061,819) is dropped for 20 minutes, continuously stirring for 15 minutes under the same temperature, then heated to 20-25° C. and reacted for an hour.

After reaction, 100 ml of chloroform is added, washed for three times (75 ml each time) with 5% sodium chloride aqueous solution, dried the organic layer over magnesium sulfate and subsequently filtered, the filtrate is refluxed and rearranged for 2 hours under the protection of nitrogen, then the solvent is removed by evaporating at reduced pressure to obtain 2.8 g (yield of 52.3%) crude products, the products are obtained by recrystallization with 30 ml of dichloromethane.

Determination of Product Structure:

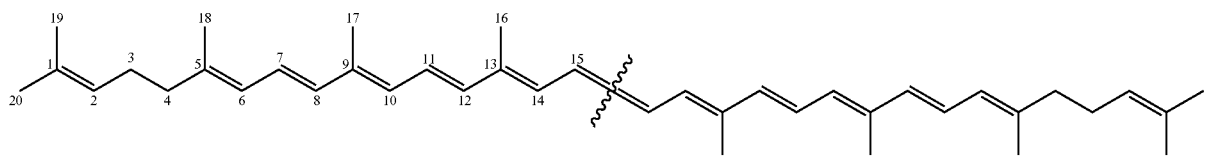

$^1$HNMR (δppm, 400 MHz, CDCl$_3$): δ 5.111, 5.975-6.943 (m, 8H, double bond H), 5.11 (m, 1H), 1.552 (S, 6H), 1.616 (S, 3H), 1.689 (S, 3H), 2.129 (S, 3H), 1.427-2.212 (m, 4H);

$^{13}$CNMR (400 MHz, CDCl$_3$) δ(ppm): 139.52 (C5); 137.37 (C12); 136.56 (C13); 136.19 (C9); 135.42 (C10); 132.66 (C14); 131.76 (C1); 131.58 (C8); 130.09 (C15); 125.73 (C11); 125.17 (C2); 124.82 (C6); 123.96 (C7); 40.25 (C4); 26.69 (C3); 25.72 (C20); 18.42 (C19); 16.97 (C18); 12.91 (C17); 12.81 (C16)

There are 13 peaks at δ(ppm) 120-140 and 7 peaks at δ(ppm) 10-45, it is determined that the product is of all trans structure with high purity.

DEPT135: 137.37; 135.42; 132.66; 131.58; 130.09; 125.73; 125.17; 124.82; 123.96; 58.48 (D); 40.25 (D); 26.69 (D); 25.72; 18.42; 16.97; 12.91; 12.81.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A method of preparing 2,6,10-trimethyl-3,5,9-undecatrienyl-1-aldehyde of formula (3), comprising the following three steps:

Step I: 3-methyl-4,4-dialkoxy-1-aldehyde of formula (11) undergoing a Wittig-Horner condensation reaction with tetra-alkyl methylene diphosphonate at temperature of 0~30° C. in ether solvent or dipolar aprotic solvent and under protection of inert gas in the presence of bases, to produce 4-methyl-5,5-dialkoxy-1-pentenyl-1-phosphoric acid dialkyl ester of formula (10); the reaction sequence is described as follows:

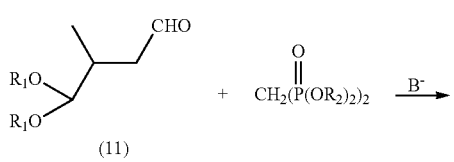

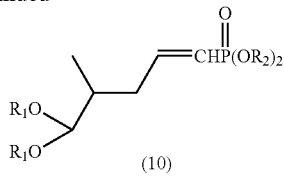

Step II comprises Step II-1 and Step II-2, wherein,

Step II-1: 4-methyl-5,5-dialkoxy-1-pentenyl-1-phosphoric acid dialkyl ester of formula (10) undergoing a rearrangement reaction at temperature of −40~30° C. in ether solvent or dipolar aprotic solvent and under protection of inert gas in the presence of bases;

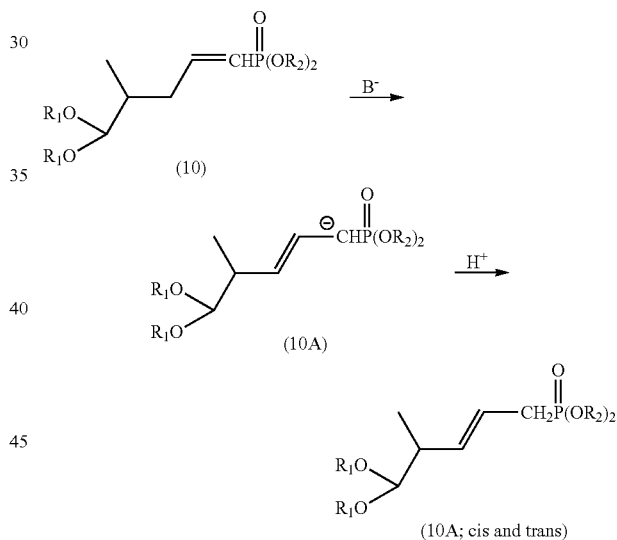

Step II-2: adding 6-methyl-5-heptene-2-one of formula (13) to the product of Step II-1 to undergo a Wittig-Horner condensation reaction at temperature of −40~30° C. in ether solvent or dipolar aprotic solvent and in the presence of bases to produce 2,6,10-trimethyl-1,1-dialkoxy-3,5,9-undecan-triene of formula (12); the reaction sequence is described as follows:

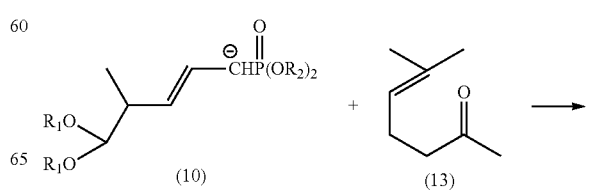

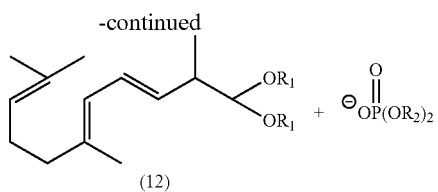

Step III: mixing-2,6,10-trimethyl-1,1-dialkoxy-3,5,9-undecan-triene of formula (12) with acid catalysts, water and homogeneous solvents to undergo a hydrolysis reaction at the temperature of 10~35 under protection of inert gas to produce 2,6,10-trimethyl-3,5,9-undecatrienyl-1-aldehyde of formula (3); the reaction sequence of Step III is described as follows:

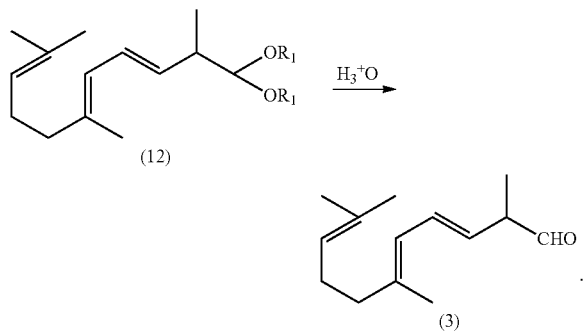

2. The method according to claim 1, characterized in that, the 4-methyl-5,5-dialkoxy-1-pentenyl-1-phosphoric acid dialkyl ester in Step I is 4-methyl-5,5-dimethoxy-1-pentenyl-1-phosphoric acid dimethyl ester, 4-methyl-5,5-dimethoxy-1-pentenyl-1-phosphoric acid diethyl ester, or 4-methyl-5,5-dimethoxy-1-pentenyl-1-phosphoric acid diisopropyl ester.

3. The method according to claim 1, characterized in that, the tetra-alkyl methylene diphosphonate in Step I is tetra-methyl methylene diphosphonate, tetra-ethyl methylene diphosphonate, or tetra-isopropyl methylene diphosphonate.

4. The method according to claim 1, characterized in that, the bases in Step I is alkali metal hydrides, alkali metal salts of alcohols or alkyl lithium; wherein the alkali metal hydride is sodium hydride or potassium hydride; the alkali metal salt of alcohols is sodium ethoxide, sodium tert-butoxide, or potassium tert-butoxidel; the alkyl lithium is butyl lithium.

5. The method according to claim 1, characterized in that, in Step I the ether solvent is ether, tetrahydrofuran or ethylene glycol dimethyl ether; the dipole aprotic solvent is dimethyl formamide, dimethyl sulfoxide, or hexamethyl-phosphoric triamide.

6. The method according to claim 1, characterized in that, in Step I a molar ratio of dosage of the 3-methyl-4,4-dialkoxy-1-aldehyde of formula (11) to the bases is 1:1.0~1.2; a molar ratio of dosage of the 3-methyl-4,4-dialkoxy-1-aldehyde of formula (11) to the tetra-alkyl methylene diphosphonate is 1:1.0~1.3.

7. The method according to claim 6, characterized in that, in Step I a molar ratio of dosage of the 3-methyl-4,4-dialkoxy-1-aldehyde of formula (11) to the bases is 1:1.0~1.1; a molar ratio of dosage of the 3-methyl-4,4-dialkoxy-1-aldehyde of formula (11) to the tetra-alkyl methylene diphosphonate is 1:1.05~1.15.

8. The method according to claim 1, characterized in that, in Step I the tetra-alkyl methylene diphosphonate firstly reacts with the bases to produce a corresponding carbanion; and then the 3-methyl-4,4-dialkoxy-1-aldehyde of formula (11) is added to undergo a Wittig-Horner condensation reaction; or in Step I the tetra-alkyl methylene diphosphonate firstly mixes with the 3-methyl-4,4-dialkoxy-1-aldehyde of formula (11) and then is added into the bases.

9. The method according to claim 1, characterized in that, the 2,6,10-trimethyl-1,1-dialkoxy-3,5,9-undecan-triene in Step II is 2,6,10-trimethyl-1,1-dimethoxy-3,5,9-undecan-triene.

10. The method according to claim 1, characterized in that, in Step II the bases is alkali metal salts of alcohols or alkyl lithium; wherein the alkali metal salt of alcohols is sodium ethoxide, sodium tert-butoxide, or potassium tert-butoxidel; the alkyl lithium is butyl lithium.

11. The method according to claim 1, characterized in that, in Step II the ether solvent is ether, tetrahydrofuran or ethylene glycol dimethyl ether; the dipole aprotic solvent is dimethyl formamide, dimethyl sulfoxide, or hexamethyl-phosphoric triamide.

12. The method according to claim 1, characterized in that, in Step II, a molar ratio of dosage of the 4-methyl-5,5-dialkoxy-1-pentenyl-1-phosphoric acid dialkyl ester of formula (10) to the bases is 1:1.0~1.2; a molar ratio of dosage of the 4-methyl-5,5-dialkoxy-1-pentenyl-1-phosphoric acid dialkyl ester of formula (10) to 6-methyl-5-heptene-2-one of formula (13) is 1:0.8~1.2.

13. The method according to claim 12, characterized in that, in Step II, a molar ratio of dosage of the 4-methyl-5,5-dialkoxy-1-pentenyl-1-phosphoric acid dialkyl ester of formula (10) to the bases is 1:1.0~1.1; a molar ratio of dosage of the 4-methyl-5,5-dialkoxy-1-pentenyl-1-phosphoric acid dialkyl ester of formula (10) to 6-methyl-5-heptene-2-one of formula (13) is 1:0.9~1.1.

14. The method according to claim 1, characterized in that, in Step II, both of the rearrangement reaction and the Wittig-Horner condensation reaction undergo at the temperature of −20~10° C.

15. The method according to claim 1, characterized in that, in Step III, the acid catalyst is sulfuric acid, p-toluene sulfonic acid, trifluoroacetic acid or amino sulfonic acid; the homogeneous solvent is tetrahydrofuran or acetone.

16. The method according to claim 1, characterized in that, in Step III, a weight ratio of dosage of the 2,6,10-trimethyl-1,1-dialkoxy-3,5,9-undecan-triene of formula (12) to the acid catalyst is 1:0.04-0.1; a ratio of dosage of the 2,6,10-trimethyl-1,1-dialkoxy-3,5,9-undecan-triene of formula (12) to the homogeneous solvent is 1:5-10 (W/V); a weight ratio of dosage of the 2,6,10-trimethyl-1,1-dialkoxy-3,5,9-undecan-triene of formula (12) to water is 1:0.8~3.2.

17. The method according to claim 1, characterized in that, further comprising that after the end of the hydrolysis reaction, sodium bicarbonate solution is firstly added into the reaction system to neutralize the reaction system until neutral, and then remove solvent via a reduced pressure evaporation, subsequently a water-immiscible organic solvent is added to extract, solvents of the organic layer is evaporated to dryness after stratification, to produce a crude product of 2,6,10-trimethyl-3,5,9-undecatrienyl-1-aldehyde of formula (3), and then refined by regular rectification to obtain a pure product of 2,6,10-trimethyl-3,5,9-undecatrienyl-1-aldehyde of formula (3).

* * * * *